US012642273B2

(12) United States Patent 
Scott et al.

(10) Patent No.: US 12,642,273 B2 
(45) Date of Patent: *Jun. 2, 2026

(54) METHODS OF PROTECTING A PLANT FROM A FUNGAL PEST

(71) Applicant: NOVOZYMES BIOAG A/S, 
Bagsvaerd (DK)

(72) Inventors: Brian R. Scott, Kanata (CA); John William Rice, Pittsboro, NC (US); Jarrod Leland, Blacksburg, VA (US); Dave Greenshields, Saskatoon (CA); Sharon Inch, Durham, NC (US)

(73) Assignee: NOVOZYMES BIOAG A/S, 
Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/776,537

(22) Filed: Jul. 18, 2024

(65) Prior Publication Data

US 2024/0365791 A1 Nov. 7, 2024

Related U.S. Application Data

(63) Continuation of application No. 16/972,983, filed as application No. PCT/US2019/035553 on Jun. 5, 2019, now Pat. No. 12,070,038.

(60) Provisional application No. 62/680,755, filed on Jun. 5, 2018.

(51) Int. Cl.

| | |
|---|---|
| *A01N 63/50* | (2020.01) |
| *A01N 25/12* | (2006.01) |
| *A01N 37/50* | (2006.01) |
| *A01N 43/40* | (2006.01) |
| *A01N 43/52* | (2006.01) |
| *A01N 43/653* | (2006.01) |
| *A01N 47/14* | (2006.01) |
| *C12N 9/42* | (2006.01) |

(52) U.S. Cl. 
CPC .............. *A01N 63/50* (2020.01); *A01N 25/12* (2013.01); *A01N 37/50* (2013.01); *A01N 43/40* (2013.01); *A01N 43/52* (2013.01); *A01N 43/653* (2013.01); *A01N 47/14* (2013.01); *C12N 9/2442* (2013.01); *C12Y 302/01014* (2013.01)

(58) Field of Classification Search 
None 
See application file for complete search history.

(56) References Cited

U.S. PATENT DOCUMENTS

| | | | |
|---|---|---|---|
| 4,762,547 | A | 8/1988 | Iwasaki et al. |
| 2013/0156740 | A1 | 6/2013 | Leland |
| 2013/0189744 | A1 | 7/2013 | Fox et al. |
| 2016/0242422 | A1 | 8/2016 | Elizer et al. |

FOREIGN PATENT DOCUMENTS

| | | |
|---|---|---|
| KR | 20020075143 A | 10/2002 |
| WO | 9413784 A1 | 6/1994 |
| WO | 9942594 A1 | 8/1999 |
| WO | 2016000671 A1 | 1/2016 |

OTHER PUBLICATIONS

Mehdiratta, Kritee, et al. "Respiratory Quinone Switches from Menaquinone to Polyketide Quinone during the Development Cycle in *Streptomyces* sp. Strain MNU77." Microbiology Spectrum 11.1 (2023): e02597-22. (Year: 2023).*
Blott, Simon J., and Kenneth Pye. "Particle size scales and classification of sediment types based on particle size distributions: Review and recommended procedures." Sedimentology 59.7 (2012): 2071-2096. (Year: 2012).*
Sun, Wenli, Mohamad Hesam Shahrajabian, and Qi Cheng. "Pyrethrum an organic and natural pesticide." Journal of Biological and Environmental Sciences 14.40 (2020): 41-44 (Year: 2020).*
Selim, Rasha E., and Mohamed S. Khalil. "Strobilurins: New group of fungicides." J. Plant Sci. Phytopathol 5.2 (2021): 63-064. (Year: 2021).*
Amicogen Co., Ltd., 2002, abstract of KR20020075143.
Hirano et al., 2016, Genbank Accession BAG22933.
Jung et al., 1999, Biotechnol. Bioprocess Eng. 4, 26-31.
Veliz et al., 2017, AIMS Microbiology 3, 689-705.

* cited by examiner

*Primary Examiner* — Robert J Yamasaki 
(74) *Attorney, Agent, or Firm* — Adam Rucker

(57) ABSTRACT

A method of controlling or preventing pathogenic damage and/or pest damage in a plant propagation material, a plant, part of a plant and/or plant organ, comprising applying on the plant, part of the plant, plant organ, plant propagation material or a surrounding area thereof a phytoprotective agent comprising an enzyme and a fungicide.

19 Claims, No Drawings 
Specification includes a Sequence Listing.

METHODS OF PROTECTING A PLANT FROM A FUNGAL PEST

CROSS-REFERENCE TO RELATED APPLICATIONS

This application is a continuation of U.S. patent application Ser. No. 16/972,983, filed Dec. 7, 2020, which is a national stage entry of PCT/US2019/035553, filed Jun. 5, 2019, which claims priority to U.S. Provisional Patent Application No. 62/680,755, filed Jun. 5, 2018. Each of the aforementioned applications is incorporated herein by reference in its entirety.

REFERENCE TO A SEQUENCE LISTING

This application contains a Sequence Listing in computer readable form, which is incorporated herein by reference. The name of the file containing the Sequence Listing is SQ.xml, which contains 2,394 bytes and which was created on Jul. 11, 2024.

BACKGROUND

Because of increasing populations and corresponding demands for more efficient and productive farms, there remains a need for new methods for protecting crops and plants from disease and pests thereby preventing waste and economic loss while improving crop yields and ensuring a sufficient global food supply.

SUMMARY OF THE CLAIMED INVENTION

The present disclosure provides methods for of controlling or preventing pathogenic damage and/or pest damage in a plant propagation material, a plant, part of a plant and/or plant organ, comprising applying on the plant, part of the plant, plant organ, plant propagation material or a surrounding area thereof a phytoprotective agent comprising an enzyme and a fungicide.

The application of a certain phytoprotective agent comprising combinations of an enzyme and a fungicide can enhance the spectrum of action with respect to the pest to be controlled, e.g. the the fungal pest. For example, the application of an agent comprising combination of enzyme and a fungicide may cause an increase in the fungicidal action of the agent which would be greater than that expected from each component when used alone. This allows, on the one hand, a substantial broadening of the spectrum of pests that can be controlled and, on the other hand, improved economics of use through lower rates of application. However, besides the actual more than additive action with respect to pest control, the methods of the invention can have further advantageous properties which can also be described, in a wider sense, as beneficial activity. Examples of such advantageous properties may include: a broadening of the spectrum of activity; a reduction in the rate of application of the active ingredient(s); adequate pest control with the aid of the compositions according to the invention, sometimes even at a rate of application at which the individual compounds are totally ineffective; advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

DETAILED DESCRIPTION

This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following description is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise.

As used herein, the terms "acaricide" and "acaricidal" refer to an agent or combination of agents the application of which is toxic to an acarid (i.e., kills an acarid, inhibits the growth of an acarid and/or inhibits the reproduction of an acarid).

As used herein, the term "agriculturally acceptable carrier" refers to a substance or composition that can be used to deliver a phytoprotective agent to a plant, plant part or plant growth medium (e.g., soil) without causing/having an unduly adverse effect on plant growth and/or yield. As used herein, the term "foliar-compatible carrier" refers to a material that can be foliarly applied to a plant or plant part without causing/having an unduly adverse effect on the plant, plant part, plant growth, plant health, or the like. As used herein, the term "seed-compatible carrier" refers to a material that can be applied to a seed without causing/having an unduly adverse effect on the seed, the plant that grows from the seed, seed germination, or the like. As used herein, the term "soil-compatible carrier" refers to a material that can be added to a soil without causing/having an unduly adverse effect on plant growth, soil structure, soil drainage, or the like.

As used herein, the term "and/or" is intended to include any and all combinations of one or more of the associated listed items, as well as the lack of combinations when interpreted in the alternative ("or"). Thus, the phrase "A, B and/or C" is to be interpreted as "A, A and B, A and B and C, A and C, B, B and C, or C."

As used herein, the terms "associated with," in association with" and "associated therewith," when used in reference to a relationship between a composition of the present disclosure and a plant or plant part, refer to at least a juxtaposition or close proximity of the composition and the plant or plant part. Such a juxtaposition or close proximity may be achieved by contacting or applying a composition directly to the plant or plant part and/or by applying the composition to the plant growth medium (e.g., soil) in which the plant or plant part will be grown (or is currently being grown). According to some embodiments, a composition is applied as a coating to the outer surface of the plant or plant part. According to some embodiments, a composition is applied to soil at, near or surrounding the site in which the plant or plant part will be grown (or is currently being grown).

As used herein, the term "aqueous" refers to a composition that contains more than a trace amount of water (i.e., more than 0.5% water by weight, based upon the total weight of the composition).

As used herein, the term "dispersant" refers to an agent or combination of agents the application of which reduces the cohesiveness of like particles, the surface tension of a liquid, the interfacial tension between two liquids and/or the interfacial tension between or a liquid and a solid.

As used herein, the terms "effective amount," "effective concentration" and "effective amount/concentration" refer to an amount or concentration that is sufficient to cause a desired effect (e.g., reduced disease severity). The absolute value of the amount/concentration that is sufficient to cause the desired effect may be affected by factors such as the type and magnitude of effect desired, the type, size and volume of material to which the composition will be applied, the type(s) of phytoprotective agent in the composition, the amount of phytoprotective agent in the composition, the stability of the phytoprotective agent in the composition and the storage conditions (e.g., temperature, relative humidity, duration). Those skilled in the art will understand how to select an effective amount/concentration using routine dose-response experiments.

As used herein, the term "foliage" refers to those portions of a plant that normally grow above the ground, including, but not limited to, leaves, stalks, stems, flowers, fruiting bodies and fruits.

As used herein, the terms "foliar application" and "foliarly applied" refer to the application of the composition of the present disclosure to the foliage of a plant (e.g., to the leaves of the plant). Application may be affected by any suitable means, including, but not limited to, spraying the plant with the composition of the present disclosure. In some embodiments, the composition of the present disclosure is/are applied to the leaves, stems and/or stalk of the plant and not to the flowers, fruiting bodies or fruits of the plant.

As used herein, the terms "fungicide" and "fungicidal" refer to an agent or combination of agents the application of which is toxic to a fungus, kills a fungus, inhibits the growth of a fungus, inhibits the reproduction of a fungus, inhibits and/or prevents spore formation by a fungus, and/or inhibits or prevents pathogenic activity by a fungus.

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a(S)-enantiomer, that embodiment also includes the (R)-enantiomer; where embodiments disclose a (R)-enantiomer, that embodiment also includes the(S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the terms "nematicide" and "nematicidal" refer to an agent or combination of agents the application of which is toxic to a nematode, kills a nematode, inhibits the growth of a nematode, inhibits the reproduction of a nematode, and/or inhibits or prevents pathogenic activity by a nematode.

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the terms "percent identity," "% identity" and "percent identical" refer to the relatedness of two or more nucleotide or amino acid sequences, which may be calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present invention, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, microbial pests, preferably bacteria and/or fungi, including oomycetes.

As used herein, the terms "pesticide" and "pesticidal" refer to agents or combinations of agents the application of which can include a fungicide or have fungicidal properties.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant. Thus, the term "plant cell" includes cells within seeds, suspension cultures, embryos, meristematic regions, callus tissue, leaves, shoots, gametophytes, sporophytes, pollen and microspores.

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds. Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated. Examples of plant propagation materials include, but are not limited to, cuttings (e.g., leaves, stems), rhizomes, seeds, tubers and cells/tissues that can be cultured into a whole plant.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

SEQ ID NO: 1 is a *Streptomyces griseus* GH18 chitinase, having an amino acide sequence:

```
MFKLHRPRARLRALAAAACTAALGATLLGVAGMSPAGATPAAQSAASPA

AAEAAPTAAGDKVIGYFTNWGTYDRNYHVKNIETSGSADKLTHINYAFG

NVIGGKCTIGDSYADYEKAYTADQSVDGVADTWDQPLRGNFNQLRKLKK

LHPDLKILWSFGGWTWSGGFGQAAQNPAAFAKSCRDLVEDPRWADVFDG

IDIDWEYPNACGLTCDTSGRDAYGNLLGELRKSFGTDLVTSAITADGSD

GGKIDAVDYAGAAKHLDWYLPMTYDFFGAWEAKGPTAPHSPLTSYPGVP

TEGENSDAAISKLKSLGIPPEKLLLGIGFYGRGWTGVTRSEPGGSATGA

AAGTYEAGIEDYRVLKNSCPATGKVAGTAYAHCGTDWWSYDTPETIGSK

MNYKNEQGLGGTFFWELSGDTGNGELIKAIR.
```

Compositions of the present disclosure may comprise any agriculturally acceptable carrier(s), including, but not limited to, foliar-compatible carriers, seed-compatible carriers and soil-compatible carriers. Selection of appropriate carrier materials will depend on the intended application(s) and the elements present in the composition. In some embodiments, the carrier material(s) will be selected to provide a composition in the form of a liquid, gel, slurry, or solid. In some embodiments, the carrier will consist essentially of or consist of one or more stabilizing compounds.

In some embodiments, the composition comprises one or more solid carriers. According to some embodiments, the composition comprises one or more powders (e.g., wettable powders) and/or granules. Non-limiting examples of solid carriers include clays (e.g., attapulgite clays, montmorillonite clay, etc.), peat-based powders and granules, freeze-dried powders, spray-dried powders, spray-freeze-dried powders and combinations thereof. In some embodiments, the composition comprises one or more liquid and/or gel carriers. According to some embodiments, the composition comprises one or more non-aqueous solvents. According to some embodiments, the composition comprises one or more aqueous solvents (e.g., water).

Compositions of the present disclosure comprising non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Compositions of the present disclosure comprising liquid enzyme preparations may, for instance, be stabilized by adding a polyol such as propylene glycol, a sugar or sugar alcohol, lactic acid or boric acid according to established methods. Compositions of the present disclosure comprising enzymes may be prepared according to the method disclosed in EP 238,216.

Compositions of the present disclosure may be formulated as a granule for example as a co-granule that combines one or more enzymes. Each enzyme will then be present in more granules securing a more uniform distribution of enzymes in, for example, a detergent. This also reduces the physical segregation of different enzymes due to different particle sizes.

An embodiment of the composition of the present disclosure relates to an enzyme granule/particle comprising an enzyme. The granule is composed of a core, and optionally one or more coatings (outer layers) surrounding the core.

Typically, the granule/particle size, measured as equivalent spherical diameter (volume based average particle size), of the granule is 20-2000 μm, particularly 50-1500 μm, 100-1500 μm or 250-1200 μm.

The core may include additional materials such as fillers, fiber materials (cellulose or synthetic fibers), stabilizing agents, solubilizing agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with an enzyme absorbed into it, or applied onto the surface, e.g., by fluid bed coating. The core may have a diameter of 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation. Methods for preparing the core can be found in Handbook of Powder Technology; Particle size enlargement by C. E. Capes; Volume 1; 1980; Elsevier. Preparation methods include known feed and granule formulation technologies, e.g.:

a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); *Powdered detergents*; Surfactant Science Series; 1998; vol. 71; page 140-142; Marcel Dekker).

b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (see also Michael S. Showell (editor); *Powdered detergents*; Surfactant Science Series; 1998; vol. 71; page 140-142; Marcel Dekker).

e) Prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also, U.S. Pat. Nos. 4,016,040 and 4,713,245 are documents relating to this technique.

f) Mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibers to reinforce the particles to give the so-called T-granulate. Reinforced particles, being more robust, release less enzymatic dust.

g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons).

h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them and form a granule.

i) The cores may be subjected to drying, such as in a fluid bed drier. The drying preferably takes place at a product temperature of from 25 to 90° C. For some embodiments of the composition of the present disclosure comprising an enzyme it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%. The coating is preferably at least 0.1 μm thick, particularly at least 0.5 μm, at least 1 μm or at least 5 μm. In a particular embodiment, the thickness of the coating is below 100 μm. In a more particular embodiment the thickness of the coating is below 60 μm. In an even more particular embodiment the total thickness of the coating is below 40 μm. In some embodiments, the coating substantially encapsulates the core unit by forming a substantially continuous layer. A substantially continuous layer is to be understood as a coating having few or no holes, so that the core unit it is encapsulating/enclosing has few or none uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 μm, such as less than 10 μm or less than 5 μm. The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminum. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°}$ $_C$.=76%), $Na_2CO_3$ ($CH_{20°}$ $_C$.=92%), $NaNO_3$ ($CH_{20°}$ $_C$.=73%), $Na_2HPO_4$ ($CH_{20°}$ $_C$.=95%), $Na_3PO_4$ ($CH_{25°}$ $_C$.=92%), $NH_4Cl$ ($CH_{20°}$ $_C$.=79.5%), $(NH_4)_2HPO_4$ ($CH_{20°}$ $_C$.=93.0%), $NH_4H_2PO_4$ ($CH_{20°}$ $_C$.=93.1%), $(NH_4)_2SO_4$ ($CH_{20°}$ $_C$.=81.1%), KCl ($CH_{20°}$ $_C$.=85%), $K_2HPO_4$ ($CH_{20°}$ $_C$.=92%), $KH_2PO_4$ ($CH_{20°}$ $_C$.=96.5%), $KNO_3$ ($CH_{20°}$ $_C$.=93.5%), $Na_2SO_4$ ($CH_{20°}$ $_C$.=93%), $K_2SO_4$ ($CH_{20°}$ $_C$.=98%), $KHSO_4$ ($CH_{20°}$ $_C$.=86%), $MgSO_4$ ($CH_{20°}$ $_C$.=90%), $ZnSO_4$ ($CH_{20°}$ $_C$.=90%) and sodium citrate ($CH_{25°}$ $_C$.=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4·7H_2O$), zinc sulfate heptahydrate ($ZnSO_4·7H_2O$), sodium phosphate dibasic heptahydrate ($Na_2HPO_4·7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

Thus, in a further aspect, a composition used in the methods of the present disclosure comprises a granule, which comprises: (a) a core comprising an enzyme, and (b) optionally a coating consisting of one or more layer(s) surrounding the core.

In some embodiments, compositions of the present disclosure are applied at a rate of about 0.5 to about 100 milliliters and/or grams of composition per plant. According to some embodiments, one or more compositions of the present disclosure is/are applied in an amount sufficient to ensure each plant is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of composition. According to some embodiments, one or more compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of composition is applied to each plant.

In some embodiments, compositions of the present disclosure are applied at a rate of about 0.5 to about 100 milliliters and/or grams of composition per acre of treated crops. According to some embodiments, one or more compositions of the present disclosure is/are applied in an amount sufficient to ensure each acre of treated crops is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of composition. According to some embodiments, one or more compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of composition is applied to each acre of treated crops.

In some embodiments, compositions of the present disclosure are applied at a rate of about 0.5 to about 100 milliliters and/or grams of composition per acre of plant growth media. According to some embodiments, one or more compositions of the present disclosure is/are applied in an amount sufficient to ensure each acre of plant growth media is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of composition. According to some embodiments, one or more compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 10, 20, 30, 40, 50, 100, 500, 1,000, 5,000, or 10,000 milliliters and/or grams of composition is applied to each acre of plant growth media.

In some embodiments, compositions of the present disclosure are applied 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and/or 100 or more days after planting.

In some embodiments, the composition comprises an enzyme derived from a strain selected from the group *Alicyclobacillus, Arthrobacter, Aspergillus* (such as *Aspergillus oryzae*), *Bacillus* (such as, *Bacillus amyloliquefaciens, Bacillus clausii, Bacillus licheniformis, Bacillus mojavensis,* and *Bacillus pumilus*), *Dichomitus squalens, Fusarium oxysporum, Janibacter, Lysobacter, Meripilus giganteus, Nocardiopsis prasina, Pyrococcus furiosus, Rhizomucor miehei, Saccharomonospora viridis, Saccharothrix aus-*

*traliensis, Saccharothrix variisporea, Streptomyces* (such as *Streptomyces violaceoruber*), *Streptosporangium albidum, Thermoascus aurantiacus, Trichoderma reesei,* and *Zophobas atratus.*

The crops of useful plants to be protected by the present invention typically comprise, for example, the following species of plants: cereals, for example wheat, barley, rye, oats, rice, maize or sorghum; beet, for example sugar or fodder beet; fruit, for example pome fruit, stone fruit and soft fruit, for example apples, pears, plums, peaches, almonds, cherries or berries, for example strawberries, raspberries and blackberries; legumes, for example beans, lentils, peas or soya beans, oil crops, for example oilseed rape, mustard, poppies, olives, sunflowers, coconut, castor-oil plants, cacao or peanuts; cucurbits, for example pumpkins, cucumbers or melons; fiber plants, for example cotton, flax, hemp or jute; citrus fruit, for example oranges, lemons, grapefruit or mandarins; vegetables, for example spinach, lettuce, asparagus, *brassica* (e.g. cabbage, broccoli, and cauliflower), carrots, onions, tomatoes, potatoes or capsicums; Lauraceae, for example avocado, Cinnamonium or camphor; or tobacco, nuts, coffee, egg plants, sugar cane, tea, pepper, grapevines, hops, Musaceae, latex plants or ornamentals (such as houseplants used in outdoor gardening or landscaping).

The present invention can be used to protect against fungal pests such as, but not limited to, anthracnose (*Colletotrichum coccodes*), corky or brown root rot (*Pyrencochaeta lycopersici*), downy mildew and late blight (*Phytophthora infestans*), early blight (*Alternaria solani*), *fusarium* crown rot (*Fusarium oxysporum*), *fusarium* wilt (*Fusarium oxyporum*), grey leaf spot (*Stemphylium solani*), grey mold (*Botrytis cinera*), gummy stem blight (*Didymella bryoniae*), head blight (*Fusarium graminearum*), leaf mold (*Fulviablva*), *phoma* rot (*Phoma destructiva*), powdery mildew (*Leveillula taurica*), *Puccinia* spp. (*P. recondita, P. striiformis, P. hordei*), Pyricularia spp., scab or gummosis (*Cladosporium cucumerinum*), *sclerotinia* stem rot (*Sclerotinia scleotiorum*), *septoria* leaf spot (*Septoria lycopersica*), *Septoria nodorum*, sheath blight (*Rhizoctonia solani*), sooty blotch (*Gloeodes pomigena*) and sudden death syndrome (*Fusarium virguliforme*), among other fungal pests. Preferably, the present invention is used to protect against Colletotricum, *Fusarium, Phytophthora, Pythium, Rhizoctonia* and/or *Sclerotinia*. Most preferably the invention is used to control *Fusarium* or *Phytophthora*.

In some embodiments, compositions of the present invention comprise one or more strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2 [2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxyimino-N-methyl-acetamide; carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyra-zole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, mandiproamid, oxytetracyclin, silthiofam and N-(6-methoxy-pyridin-3-yl) cyclopropanecarboxylic acid amide; azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf.D1b), 3-[5-(4-chloro-phenyl)-2,3-dimethyl-isoxazolidin-3-yl]-pyridine, 3-[5-(4-methyl-phenyl)-2,3-di-methyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin), dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A); nitrophenyl derivates (e.g., binapacryl, dicloran, dinobuton, dinocap, nitrothal-isopropyl, tecnazen); organometal compounds (e.g., fentin salts, such as fentin-acetate, fentin chloride, fentin hydroxide); sulfur-containing heterocyclyl compounds (e.g., dithianon, isoprothiolane); organophosphorus compounds (e.g., edifenphos, fosetyl, fosetyl-aluminum, iprobenfos, phosphorus acid and its salts, pyrazophos, tolclofos-methyl); organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanate, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In some embodiments, compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole. In some embodiments, compositions of the present disclosure comprise azoxystrobin, pyraclostrobin, fluoxastrobin, trifloxystrobin, ipconazole, prothioconazole, sedaxane, fludioxonil, metalaxyl, mefenoxam, thiabendazole, fluxapyroxad and/or fluopyram. In some embodiments, compositions of the present disclosure comprise one or more aromatic hydrocarbons, benzimidazoles, o, carboxamides, carboxylic acid amides, morpholines, phenylamides, phosphonates, quinone outside inhibitors (e.g. strobilurins), thiazolidines, thiophanates, thiophene carboxamides and/or triazoles The present invention is further described by the following numbered paragraphs:

Paragraph [1]. A method comprising foliar application of a composition comprising an effective amount of a phytoprotective agent to a plant and/or plant part.

Paragraph [2]. A method of controlling plant pests in a plant or plant part and/or inducing resistance to a plant pest in a plant or plant part, comprising applying an effective amount of a composition comprising a phytoprotective agent to the plant or plant part.

Paragraph [3]. The method of controlling or preventing pest damage in a plant propagation material, a plant, part of a plant and/or plant organ, comprising applying on the plant, part of the plant, plant organ, plant propagation material or a surrounding area thereof an effective amount of a composition comprising a phytoprotective agent.

Paragraph [4]. The method of any one of paragraphs 1-3, wherein the phytoprotective agent comprises an enzyme.

Paragraph [5]. The method of any one of paragraphs 1-3, wherein the phytoprotective agent comprises a polypeptide having at least 70%, 75%, 80%, 81%, 82%, 83%, 84%, 85%, 86%, 87%, 88%, 89%, 90%, 91%, 92%, 93%, 94%, 95%, 96%, 97%, 97.5%, 98% 98.5%, 99%, 99.5%, or 100% sequence identity with a sequence selected from the group SEQ ID NO: 1.

Paragraph [6]. The method of any one of paragraphs 1-3, wherein the phytoprotective agent comprises:

a. an enzyme, optionally having chitin-degrading, chitin deacetylase, chitosanase, chitinase, cutinase, beta-glucanase, beta-1,4-glucanase, beta-1,3-glucanase, lipase, lytic polysaccharide monooxygenase, copper radical oxidase, oxidoreductase, protease, haloperoxidase, peroxygenase, mannose-degrading, alpha-mannosidase, expansin, and/or polygalactose-aminidase activity, optionally derived from a strain selected from the group *Alicyclobacillus, Arthrobacter, Aspergillus oryzae, Bacillus* (such as, *Bacillus amyloliquefaciens, Bacillus clausii, Bacillus licheniformis, Bacillus mojavensis,* and *Bacillus pumilus*), *Dichomitus squalens, Fusarium oxysporum, Janibacter, Lysobacter, Meripilus giganteus, Nocardiopsis prasina, Pyrococcus furiosus, Rhizomucor miehei, Saccharomonospora viridis, Saccharothrix australiensis, Saccharothrix variisporea, Streptomyces* (such as *Streptomyces violaceoruber*), *Streptosporangium albidum, Thermoascus aurantiacus, Trichoderma reesei,* and *Zophobas atratus*; and b. a fungicide, optionally one or more aromatic hydrocarbons, benzimidazoles, benzothiadiazole, carboxamides, carboxylic acid amides, morpholines, phenylamides, phosphonates, quinone outside inhibitors, thiazolidines, thiophanates, thiophene carboxamides and/or triazoles.

Paragraph [7]. The method of any one of paragraphs 1-6, wherein the phytoprotective agent further comprises one or more acaricides, insecticides and/or nematicides, optionally one or more carbamates, diamides, macrocyclic lactones, neonicotinoids, organophosphates, phenylpyrazoles, pyrethrins, spinosyns, synthetic pyrethroids, tetronic acids and/or tetramic acids.

Paragraph [8]. The method of any one of paragraphs 1-7, wherein the plant part is foliage.

Paragraph [9]. The method of any one of paragraphs 1-8, wherein the phytoprotective agent is in an amount/concentration of about 0.0001 to about 95% or more (by weight) of the composition, for example about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 10, 15, 20, 25, 30, 35, 40, 45, 50, 55, 60, 65, 70, 75, 80, 85, 90, 95%. (by weight) of the composition.

Paragraph [10]. The method of any one of paragraphs 1-9, wherein the composition further comprises an agriculturally acceptable carrier, for example, a foliar-compatible carrier, a seed-compatible carrier, and/or a soil-compatible carrier, wherein the carrier comprises a liquid, gel, slurry, or solid, optionally:

one or more monosaccharides, optionally arabinose, fructose and/or glucose;

one or more disaccharides, optionally maltose, sucrose and/or trehalose;

one or more maltodextrins, optionally one or more maltodextrins (e.g., one or more maltodextrins (each and/or collectively) having a DEV value of about 15 to about 20;

one or more sugar alcohols, optionally arabitol, mannitol, sorbitol and/or xylitol;

one or more humic acids, optionally potassium humate and/or sodium humate;

one or more fulvic acids, optionally potassium fulvate and/or sodium fulvate;

one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches;

one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate; and/or one or more UV protectants, optionally one or more lignosulfites.

Paragraph [11]. The method of any one of paragraphs 1-10, wherein the composition further comprises one or more gastropodicides, optionally one or more iron phosphates, metaldehydes, methiocarbs and/or salts;

one or more herbicides, optionally one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, and/or nucleic acid inhibitors;

one or more rodenticides, optionally brodifacoum, bromadiolone, bromethalin, cholecalciferol, chlorophacinone, difethialone, diphacinone, strychnine, warfarin and/or zinc phosphide; and/or one or more virucides.

Paragraph [12]. The method of any one of paragraphs 1-11, wherein the composition further comprises one or more flavonoids, optionally:

one or more anthocyanidins, optionally cyanidin, delphinidin, malvidin, pelargonidin, peonidin and/or petunidin;

one or more anthoxanthins, optionally one or more flavones, such as apigenin, baicalein, chrysin, 7,8-dihydroxyflavone, diosmin, flavoxate, 6-hydroxyflavone, luteolin, scutellarein, tangeritin and/or wogonin; and/or flavonols, such as amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin;

one or more flavanones, optionally butin, eriodictyol, hesperetin, hesperidin, homoeriodictyol, isosakuranetin, naringenin, naringin, pinocembrin, poncirin, sakuranetin, sakuranin and/or sterubin;

one or more flavanonols, optionally dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or one or more isoflavonoids, optionally one or more isoflavones, such as biochanin A, daidzein, formononetin, genistein and/or glycitein; isoflavanes, such as equol, ionchocarpane and/or laxifloorane; isoflavandiols; isoflavenes, such asglabrene, haginin D and/or 2-methoxyjudaicin; coumestans, such as coumestrol, plicadin and/or wedelolactone; pterocarpans; and/or roetonoids; and/or one or more neoflavonoids, optionally calophyllolide, coutareagenin, dalbergichromene, dalbergin and/or nivetin; and/or one or more pterocarpans, optionally bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin.

Paragraph [13]. The method of any one of paragraphs 1-12, wherein the composition further comprises one or more water-soluble anionic surfactants and/or one or more water-insoluble anionic surfactants, optionally: one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

Paragraph [14]. The method of any of one of paragraphs 1-13, wherein the composition further comprises one or more cationic surfactants, optionally: alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride.

Paragraph [15]. The method of any one of paragraphs 1-14, wherein the composition further comprises one or more water-soluble nonionic surfactants and/or one or more water-insoluble nonionic surfactants, optionally: alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

Paragraph [16]. The method of any one of paragraphs 1-15, wherein the composition further comprises one or more zwitterionic surfactants, optionally: 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidyl-
choline and/or one or more sphingomyelins.

Paragraph [17]. The method of any one of claims 1-16,
wherein the composition further comprises one or more
soaps and/or organosilicone surfactants, optionally: one or
more alkali metal salts of fatty acids.

Paragraph [18]. A method of any one of paragraphs 1-9,
wherein the composition comprises a granule comprising
one or more enzymes, optionally wherein the granule has an
average particle size of 20-2000 μm equivalent spherical
diameter.

Paragraph [19]. A method of paragraph 18, wherein the
composition comprises a core and optionally one or more
coatings surrounding the core, wherein the core optionally
comprises:

one ore more additional materials such as fillers, fiber
materials (cellulose or synthetic fibers), stabilizing
agents, solubilizing agents, suspension agents, viscos-
ity regulating agents, light spheres, plasticizers, salts,
lubricants and fragrances;

one or more binders, such as synthetic polymer, wax, fat,
or carbohydrate;

one ore more of a salt of a multivalent cation, a reducing
agent, an antioxidant, a peroxide decomposing catalyst
and/or an acidic buffer component, optionally as a
homogenous blend;

one ore more of an inert particle with an enzyme absorbed
into it, or applied onto the surface, for example, by fluid
bed coating.

Paragraph [20]. The method of any one of paragraphs
1-19, whereby the pest infestation severity and/or pest
damage is reduced by at least about 5%, 10%, 15%, 20%,
25%, 30%, 35%, 40%, 45%, 50%, 55%, 60%, 65%, 70%,
75%, 80%, 85%, 90%, 95%, 96%, 97%, 98%, 99%, or 100%
compared to a plant that has not had the phytoprotective
agent applied.

Paragraph [21]. The method of any one of paragraphs
1-20, wherein the composition is applied 1, 2, 3, 4, 5, 6, 7,
8, 9, 10, 11, 12, 13, 14, 15, 16, 17, 18, 19, 20, 21, 22, 23, 24,
25, 26, 27, 28, 29, 30, 31, 32, 33, 34, 35, 36, 37, 38, 39, 40,
41, 42, 43, 44, 45, 46, 47, 48, 49, 50, 51, 52, 53, 54, 55, 56,
57, 58, 59, 60, 61, 62, 63, 64, 65, 66, 67, 68, 69, 70, 71, 72,
73, 74, 75, 76, 77, 78, 79, 80, 81, 82, 83, 84, 85, 86, 87, 88,
89, 90, 91, 92, 93, 94, 95, 96, 97, 98, 99, and/or 100 days or
more after planting.

EXAMPLES

The following examples are not intended to be a detailed
catalogue of all the different ways in which the present
disclosure may be implemented or of all the features that
may be added to the present disclosure. Subjects skilled in
the art will appreciate that numerous variations and addi-
tions to the various embodiments may be made without
departing from the present disclosure. Hence, the following
descriptions are intended to illustrate some particular
embodiments of the invention and not to exhaustively
specify all permutations, combinations and variations
thereof.

In the following examples, Composition 1 comprises an
enzyme having the polypeptide sequence of SEQ ID NO: 1.
In one or more examples, Composition 1 and/or one or more
other compositions comprise an enzyme having chitin-
degrading, chitin deacetylase, chitosanase, chitinase, cuti-
nase, beta-glucanase, beta-1,4-glucanase, beta-1,3-gluca-
nase, lipase, lytic polysaccharide monooxygenase, copper
radical oxidase, oxidoreductase, protease, haloperoxidase, peroxygenase, mannose-degrading, alpha-mannosidase,
expansin, and/or polygalactose-aminidase activity. In one or
more examples, the composition and/or fungicide comprises
a strobilurin fungicide, a sterol biosynthesis inhibiting fun-
gicde, a succinate dehydrogenase inhibitor fungicide, a
copper fungicide, a phenylamine fungicide, and/or a phthal-
imide fungicide. In one or more examples, the composition
and/or fungicide comprises azoxystrobin, pyraclostrobin,
trifloxystrobin, prothioconazole, tebuconazole, spiroxamine,
boscalid, bixafen, copper, metalaxyl, and/or chlorothalonil.
In one or more examples, the pathogen and/or spores com-
prise sordariomycetes, hypocreales, omycetes, peronospo-
rales, teliomycetes, uredinales, dothdeomycetes, pleospo-
rales, *Fusarium graminearum, Fusarium oxysporum,
Fusarium virguliforme, Phytophthora infestans, Puccinia
graminis*, and/or *Septoria nodorum*.

Example 1: DNA Cloning and Enzyme Expression

Experimental enzymes were cloned into either *B. subtilis*
or *A. oryzae* using standard methods (reference?). *B. subtilis*
cloned enzymes typically were cloned in frame with an
N-terminal 6-Histidine tag to facilitate purification. Expres-
sion for *B. subtilis* strains was performed in the following
manner: cultures were plated on LBPSG+6cam and incu-
bated overnight. A single isolated colony was selected to
inoculate 5 mL of LB+6cam or similar media and incubated
at 37° C. for 5 hr with shaking at 225 rpm. 1 mL of culture
was then used to inoculate 400-3000 mL of 10R-av-30CS,
Cal-18+cam or similar media in a baffled shakeflask and
incubated for 3 days at 26-30° C., shaking at 225-250 rpm.
Expression for *A. oryzae* strains was performed in the
following manner: 1 mL of spore culture was used to
inoculate 800-1200 mL of YP+2% glucose, Dap4C media,
and incubated at 30° C. for 5 days with shaking at 80 rpm.
Cultures were harvested by centrifugation at 10000 rpm for
30 minutes and were sterile-filtered using a 0.2 μm PES filter
(VWR®). Expression was assessed by SDS-PAGE.

Example 2: Enzyme Purification

Sterile-filtered broths were purified using standard meth-
ods. Briefly, His6-tagged enzymes were purified by Ni-
affinity (IMAC) chromatography using a 5 mL His-trap
Excel (GE® Life Sciences) column according to standard
protocols, eluting with 800 mM imidazole. Purified enzyme
was buffer exchanged into 50 mM HEPES, 100 mM NaCl
pH 7.0 or 20 mM Tris, pH 7.0 using Sephadex G25 column
(GE® Life Sciences). Enzymes without a His6-tag were
typically purified using hydrophobic interaction chromatog-
raphy (HIC). 1.8M ammonium sulfate was first added to the
broth, then the solution was applied to a 5 mL phenyl
sepharose column before eluting with a step gradient of 50%
ethanol. Eluted enzyme was desalted as described above.
Purification was assessed by SDS-PAGE and concentration
was determined by A280 or Qubit analysis according to
manufacturer's protocols.

Example 3: Preparation of Fungal Spores a) *Fusarium virguliforme* Spore Suspension Preparation One half strength V8 plates of *F. virguliforme* (isolate
37592) were grown for 10 days at room temperature under
fluorescent lighting. A spore suspension was prepared by
flooding the plate with 2 mL of M9 media. The spores were
gently scraped from the surface, filtered through 2 layers of
sterile cheesecloth, and spore concentration was determined using a hemocytometer. The final spore suspension was adjusted to $1\times10^5$ spore per mL using M9 media.

b) *Fusarium graminearum* Spore Suspension Preparation

A spore suspension of *Fusarium graminearum* was prepared by inoculating 50 mL of CMC media (carboxymethyl cellulose 15 g, $NH_4NO_3$ 1 g, $KH_2PO_4$ 1 g, $MgSO_4\_7H_2O$ 0.5 g, yeast extract 1 g, distilled water 1 L and streptomycin sulfate 0.2 g added to the cooled medium) with 5-day old PDA plates of *F. graminearum* (isolate 8-13). The inoculated vented 125 mL Erlenmeyer flasks were incubated at 24° C. at 200 rpm for 7 days. After 7 days, the culture was filtered through 2 layers of sterile cheese cloth and centrifuged for 5 mins at 2000 rpm. The supernatant was removed and the spores were re-suspended in M9 media. The spore concentration was enumerated using a hemocytometer and the concentration was adjusted using M9 to $1.5\times10^5$ spores per mL.

c) *Septoria nodorum*

Full strength V8 plates of *S. nodorum* were grown for 17 days at room temperature under fluorescent lighting. A spore suspension was prepared by flooding the plate with 2 mL of M9 media. The spores were gently scraped from the surface, filtered through 2 layers of sterile cheesecloth, and spore concentration was determined using a hemocytometer. The final spore suspension was adjusted to $1\times10^5$ spore per mL using M9 media.

Example 4: High Content Imaging Assay for Reduced Fungal Spore Germination and/or Growth All tested chemical fungicides were prepared from 10 mM DMSO stocks, and all enzyme samples were desalted and buffer exchanged into M9 media formulation. Test samples, either enzyme alone or in combination with chemical fungicides, were made up at a 2x concentration and were transferred into a 384-well assay plate. An equal volume of test pathogen spores diluted in M9 media formulation to 15,000 spores/mL was then added. Following a 48-hour incubation at room temperature, a fixative/dye solution made up of 95% methanol, 5% glacial acetic acid and 5-10 µM of either SytoBC or FUN1 fluorescent dye were added to the test samples. Following an additional ~2-hour room temperature incubation, the 384-well assay plates were imaged using an InCell 2200 high content analysis system. Images were cropped in ImageJ to remove well edges, and the cropped images were analyzed to detect hyphal length via fluorescent intensity using GE® developer image analysis software. Percent hyphal growth inhibition was calculated by normalization of all test samples to either an untreated negative control or to a control containing an equivalent concentration of chemical fungicide as the test sample, and to a positive inhibition control consisting of 100 µg/mL cycloheximide. Enzyme concentrations in these experiments ranged from 10 µg/mL to 1 mg/mL. Results with prothioconazole as the chemical fungicide, where target fungal organism *F. graminearum* is denoted G and *F. virguliforme* is denoted V, are shown in Table 1 and Table 2.

TABLE 1

| Enzyme | Activity | Target | % mycelial reduction |
|---|---|---|---|
| A | chitinase | G | 59.6 |
| | | F | 10.0 |
| B | chitinase | G | 28.9 |
| | | F | 54.0 |

TABLE 1-continued

| Enzyme | Activity | Target | % mycelial reduction |
|---|---|---|---|
| C | chitinase | G | 25.9 |
| | | F | 58.0 |
| D | chitinase | G | 28.8 |
| | | F | 59.7 |
| E | chitinase | G | 32.2 |
| | | F | 50.3 |
| F | chitinase | G | 53.3 |
| | | F | 82.3 |
| G | chitinase | G | 7.1 |
| | | F | 46.4 |
| H | chitinase | G | 33.8 |
| | | F | 77.5 |
| I | lysozyme | G | 12.4 |
| | | F | 54.4 |
| J | chitin deacetylase | G | 35.8 |
| | | F | 67.4 |
| K | chitosanase | F | 52.1 |
| L | chitosanase | G | 66.0 |
| | | F | 16.6 |
| M | chitosanase | G | 29.0 |
| | | F | 64.4 |
| N | chitosanase | G | 23.8 |
| | | F | 99.2 |
| O | beta-1,6-glucanase | F | 0.1 |
| P | beta-1,6-glucanase | G | 11.1 |
| | | F | 30.7 |
| Q | beta-1,3-glucanase | G | 38.2 |
| | | F | 13.9 |
| R | beta-1,6-glucanase | G | 37.8 |
| | | F | 97.5 |
| S | beta-1,6-glucanase | G | 40.7 |
| | | F | 97.8 |
| T | chitin beta-1,6-glucanosyltransferase | G | 56.2 |

TABLE 2

| Enzyme | Activity | Target | % mycelial reduction |
|---|---|---|---|
| U | alpha-1,3-glucanase | G | 61.8 |
| | | F | 66.1 |
| V | alpha-1,3-glucanase | G | 9.6 |
| | | F | 80.5 |
| W | beta-1,3-glucanase | G | 48.2 |
| | | F | 96.1 |
| X | alpha-1,6-mannanase | G | 89.1 |
| | | F | 94.6 |
| Y | alpha-1,2-mannosidase | G | 55.8 |
| | | F | 7.6 |
| Z | dextranase | G | 32.9 |
| | | F | 90.7 |
| AA | dextranase | G | 27.3 |
| AB | alpha-1,6-glucanase | G | 12.7 |
| | | F | 89.8 |
| AC | alpha-1,6-glucanase | G | 23.2 |
| | | F | 88.4 |
| AD | alpha-1,4-polygalactosaminidase | G | 22.1 |
| | | F | 96.5 |
| AE | alpha-1,4-polygalactosaminidase | G | 32.3 |
| | | F | 96.9 |
| AF | galactosaminogalactanase | G | 25.4 |
| | | F | 92.9 |
| AG | galactosaminogalactanase | G | 40.3 |
| | | F | 88.1 |
| AH | galactosaminogalactanase | G | 60.4 |
| | | F | 93.9 |
| AI | galactosaminogalactanase | G | 46.0 |
| | | F | 91.2 |
| AJ | galactosaminogalactanase | G | 30.7 |
| | | F | 86.6 |
| AK | galactosaminogalactanase | G | 28.7 |
| | | F | 97.8 |
| AL | galactosaminogalactanase | G | 8.7 |
| | | F | 92.5 |

TABLE 2-continued

| Enzyme | Activity | Target | % mycelial reduction |
|--------|----------|--------|----------------------|
| AM | beta-N-acetylhexosaminidase | G | 56.9 |
| | | F | 30.6 |
| AN | glyoxal oxidase | G | 66.8 |
| | | F | 87.3 |
| AO | alpha-1,4-polygalactosaminidase | F | 57.7 |
| AP | expansin | G | 47.6 |
| | | F | 89.3 |

Additive effectiveness of enzymes and chemical fungicide was identified by titration of enzyme at a fixed fungicide concentration. A serial dilution of enzyme between 1 µg/mL and 1 mg/mL final concentration was used to determine inhibitory enzyme concentrations, and additive effectiveness was quantified by comparing $EC_{50}$ values of enzyme treatments alone to enzyme+chemistry treatments. An enzyme/chemistry combination displaying an $EC_{50}$ concentration at least 2-fold lower in combination with chemistry than enzyme alone was considered to display greater than additive activity. Results are shown in Table 3.

TABLE 3

| Activity | Pathogen | EC50 Enzyme (mg/ml) | IC50 plus chemistry (mg/ml) | Chemical Fungicide |
|----------|----------|---------------------|------------------------------|---------------------|
| beta-1,6-glucanase | *Fusarium graminearum* | 0.403 | >0.5 | 20 uM Prothioconazole |
| alpha-1,6-mannanase | *Septoria nodorum* | 0.02048 | 0.2278 | 0.2 uM Prothioconazole |
| | *Fusarium graminearum* | 0.08056 | 0.1162 | 20 uM Prothioconazole |
| | *Fusarium virguliforme* | 0.1032 | 0.08444 | 20 uM Prothioconazole |
| chitinase | *Septoria nodorum* | >0.5 | 0.36 | 0.2 uM Prothioconazole |
| | *Fusarium graminearum* | >0.5 | 0.36 | 20 uM Prothioconazole |
| expansin | *Septoria nodorum* | 0.294 | >0.5 | 0.2 uM Prothioconazole |
| chitinase | *Fusarium virguliforme* | >0.5 | 0.02817 | 20 uM Prothioconazole |
| Galacto-saminogalactanase | *Septoria nodorum* | 0.124 | >0.5 | 0.2 uM Prothioconazole |
| | *Fusarium virguliforme* | 0.02086 | 0.02581 | 0.25 uM Benomyl |
| lysozyme | *Fusarium virguliforme* | >0.5 | 0.002 | 20 uM Prothioconazole |
| chitinase | *Fusarium virguliforme* | >0.5 | 0.009 | 20 uM Prothioconazole |
| | *Fusarium virguliforme* | >0.5 | 0.001486 | 20 uM Prothioconazole |
| beta-N-acetylhexosaminidase | *Septoria nodorum* | 0.1586 | >0.5 | 0.2 uM Prothioconazole |
| Galacto-saminogalactanase | *Septoria nodorum* | 0.182 | >0.5 | 0.2 uM Prothioconazole |
| | *Fusarium virguliforme* | 0.03 | 0.06 | 0.5 uM Fluopyram |
| | *Fusarium virguliforme* | 0.03 | 0.02 | 0.25 uM Benomyl |
| alpha-1,6-glucanase | *Septoria nodorum* | 0.1657 | >0.5 | 0.2 uM Prothioconazole |
| alpha-1,4-polygalactosaminidase | *Septoria nodorum* | 0.092 | >0.5 | 0.2 uM Prothioconazole |
| | *Fusarium graminearum* | >0.5 | 0.511 | 20 uM Prothioconazole |
| beta-1,6-glucanase | *Fusarium graminearum* | >0.5 | 0.21 | 20 uM Prothioconazole |
| | *Septoria nodorum* | >0.5 | 0.06519 | 0.25 uM Benomyl |
| beta-1,6-glucanase | *Septoria nodorum* | 0.135 | >0.5 | 0.2 uM Prothioconazole |
| | *Fusarium graminearum* | >0.5 | 0.194 | 20 uM Prothioconazole |
| chitin deacetylase | *Fusarium graminearum* | >0.5 | 0.185 | 20 uM Prothioconazole |
| chitinase | *Septoria nodorum* | 0.2595 | >0.5 | 0.2 uM Prothioconazole |
| chitinase | *Fusarium virguliforme* | 0.02 | 0.005 | 5 uM Chlorothalonil |
| | *Fusarium virguliforme* | 0.02 | >0.5 | 0.5 uM Fluopyram |
| | *Fusarium virguliforme* | 0.02 | 0.05 | 0.5 uM Benomyl |
| | *Septoria nodorum* | 0.1825 | >0.5 | 0.2 uM Prothioconazole |
| chitosanase | *Septoria nodorum* | 0.1352 | >0.5 | 0.2 uM Prothioconazole |
| beta-1,6-glucanase | *Fusarium graminearum* | >0.5 | 0.086 | 20 uM Prothioconazole |
| alpha-amylase | *Fusarium virguliforme* | 0.192 | >0.5 | 20 uM Prothioconazole |
| catalase | *Septoria nodorum* | 0.285 | >0.5 | 0.2 uM Prothioconazole |
| glucose oxidase | *Botrytis cinerea* | <0.001 | <0.001 | 0.2 uM Prothioconazole |
| | *Septoria nodorum* | <0.001 | <0.001 | 0.2 uM Prothioconazole |
| | *Fusarium graminearum* | <0.001 | <0.001 | 20 uM Prothioconazole |
| | *Fusarium virguliforme* | <0.001 | <0.001 | 20 uM Prothioconazole |

Example 5: MTT Cell Viability Assay for Reduced Fungal Spore Germination and/or Growth Assays were carried out in 1.5 mL microcentrifuge tubes. The indicated fungicides were dissolved in DMSO at a stock concentration of 1 mg/mL. Enzymes were desalted into 50 mM MES buffer, pH 6.0 using a 200 mL Sephadex G25 column with 9.5 mL/min flowrate before adding to the germination assay. The germination assay consisted of potato dextrose broth media, fungicide at the $IC_{50}$ concentration or no fungicide, with or without enzyme at a concentration of 200 µg/mL, and fungal spores at a titer of $10^6$/mL in a final volume of 400 µl. The reaction mixture without fungicide served as a negative inhibition control, and a reaction mixture containing 0.2 mg/mL mannase acid or 20 mg/mL M-PEG (1,2-propanediol) served as a positive inhibition control. The spore germination mixture was incubated at 27° C. for 3 days. At the end of the incubation period, 200 µL of 3-(4,5-dimethylthiazol-2-yl)-2,5-diphenyltetrazolium bromide (MTT) dye was added to the existing 400 µL of assay culture and was incubated for another 3 hr at 27° C. in the dark. The tubes were then centrifuged, and the supernatants were discarded. To the residue left in the tubes, 200 µL of DMSO was added to dissolve the formazan formed by the live fungal cells. The tubes were vortexed and centrifuged again. 100 µL of the supernatant from each tube was transferred into a separate well in a 96-well microtiter plate and absorbance was measured at 540 nm. Inhibition of fungal germination and growth by enzymes was determined relative to the uninhibited control for samples without chemical fungicide, and relative to the 50% inhibited cultures for samples containing each of the chemical fungicides tested. Results are shown in Table 4 and Table 5.

TABLE 4

| Enzyme | Activity | Target Fungus | Fungicide | % inhibition |
|---|---|---|---|---|
| BA | glucose oxidase | *F. verticilloides* | none | 88.02 |
| | | *F. verticilloides* | antracol | 95.29 |
| | | *F. verticilloides* | prothioconazole | 92.87 |
| | | *C. gleosporoides* | none | 69.06 |
| | | *C. gleosporoides* | antracol | 84.65 |
| BB | blend | *F. verticilloides* | antracol | 1.1 |
| | | *F. verticilloides* | prothioconazole | 9.61 |
| | | *C. gleosporoides* | antracol | 4.73 |
| BC | blend | *F. verticilloides* | none | 45.24 |
| | | *F. verticilloides* | antracol | 32.24 |
| | | *F. verticilloides* | prothioconazole | 98.13 |
| | | *C. gleosporoides* | none | 76.59 |
| | | *C. gleosporoides* | antracol | 83.48 |
| BD | dextranase | *F. verticilloides* | none | 32 |
| | | *F. verticilloides* | antracol | 26.34 |
| | | *F. verticilloides* | prothioconazole | 79.61 |
| | | *C. gleosporoides* | none | 25.11 |
| | | *C. gleosporoides* | antracol | 54.18 |
| BE | alpha-amylase | *F.verticilloides* | prothioconazole | 34.14 |
| BF | cellulase | *F. verticilloides* | prothioconazole | 23.01 |

TABLE 4-continued

| Enzyme | Activity | Target Fungus | Fungicide | % inhibition |
|---|---|---|---|---|
| BG | protease | *F. verticilloides* | none | 8.54 |
| | | *F. verticilloides* | antracol | 2.88 |
| | | *F. verticilloides* | prothioconazole | 2.01 |
| | | *C. gleosporoides* | antracol | 14.59 |
| BH | blend | *F. verticilloides* | antracol | 9.23 |
| | | *F. verticilloides* | prothioconazole | 1.74 |
| | | *C. gleosporoides* | antracol | 21.89 |
| BI | blend | *F. verticilloides* | none | 0.99 |
| | | *F. verticilloides* | prothioconazole | 5.57 |
| | | *C. gleosporoides* | antracol | 10.48 |
| BJ | blend | *F. verticilloides* | antracol | 3.34 |
| | | *C. gleosporoides* | none | 15.84 |
| | | *C. gleosporoides* | antracol | 13.54 |
| BK | glucoamylase | *C. gleosporoides* | antracol | 6.83 |
| BL | amylase | *C. gleosporoides* | antracol | 17.57 |
| BM | beta-glucanase, xylanase | *C. gleosporoides* | antracol | 12.82 |
| BN | chitinase | *F. verticilloides* | prothioconazole | 11.37 |
| | | *F. verticilloides* | trifloxystrobin | 21.8 |
| | | *C. gleosporoides* | none | 11.6 |
| | | *C. gleosporoides* | antracol | 21.5 |
| BO | chitinase | *F. verticilloides* | prothioconazole | 10 |
| BP | alpha-1,3-glucanase | *F. verticilloides* | prothioconazole | 9.86 |
| | | *F. verticilloides* | trifloxystrobin | 18.64 |
| | | *C. gleosporoides* | none | 13.49 |
| | | *C. gleosporoides* | antracol | 30.55 |

TABLE 5

| Enzyme | Activity | Target Fungus | Fungicide | % inhibition |
|---|---|---|---|---|
| BQ | alpha-1,3-glucanase | *F. verticilloides* | antracol | 42.18 |
| | | *C. gleosporoides* | antracol | 9.06 |
| BR | chitosanase | *F. verticilloides* | antracol | 34.6 |
| | | *C. gleosporoides* | antracol | 4.54 |
| BS | chitinase | *F. verticilloides* | trifloxystrobin | 31.14 |
| | | *C. gleosporoides* | antracol | 40.03 |
| | | *C. gleosporoides* | none | 1.87 |
| BT | beta-1,4-chitinase | *F. verticilloides* | trifloxystrobin | 39.55 |
| | | *C. gleosporoides* | none | 8.21 |
| | | *C. gleosporoides* | antracol | 39.84 |
| BU | beta-1,3(4)-glucanase | *C. gleosporoides* | antracol | 39.32 |
| | | *C. gleosporoides* | none | 9.86 |
| BV | beta-1,6-glucanase | *F. verticilloides* | antracol | 9.64 |
| | | *F. verticilloides* | trifloxystrobin | 29.01 |
| | | *C. gleosporoides* | none | 5.66 |
| BW | alpha-1,2-mannosidase | *F. verticilloides* | antracol | 7.93 |
| | | *F. verticilloides* | trifloxystrobin | 9.83 |
| | | *C. gleosporoides* | none | 10.95 |
| | | *C. gleosporoides* | antracol | 22.06 |
| BX | chitosanase | *F. verticilloides* | trifloxystrobin | 8.45 |
| | | *C. gleosporoides* | none | 9.05 |
| | | *C. gleosporoides* | antracol | 26.75 |
| BY | chitosanase | *F. verticilloides* | prothioconazole | 8.7 |
| | | *F. verticilloides* | trifloxystrobin | 4.33 |
| | | *C. gleosporoides* | none | 11.75 |
| | | *C. gleosporoides* | antracol | 33.02 |
| BZ | chitosanase | *F. verticilloides* | trifloxystrobin | 3.49 |
| | | *C. gleosporoides* | antracol | 6.77 |
| CA | chitinase | *F. verticilloides* | antracol | 13.49 |
| | | *F. verticilloides* | trifloxystrobin | 3.26 |
| CB | chitinase | *F. verticilloides* | antracol | 3.54 |
| | | *F. verticilloides* | trifloxystrobin | 3.2 |
| CD | beta-N-acetylhexosaminidase | *F. verticilloides* | trifloxystrobin | 67.92 |
| CE | alpha-1,4-polygalactosaminidase | *F. verticilloides* | trifloxystrobin | 40.89 |
| CF | alpha-1,4-polygalactosaminidase | *F. verticilloides* | trifloxystrobin | 16.3 |
| CG | alpha-1,4-polygalactosaminidase | *F. verticilloides* | trifloxystrobin | 16.2 |
| CH | alpha-1,4-polygalactosaminidase | *F. verticilloides* | trifloxystrobin | 13.74 |
| CI | chitin beta-1,6-glucanosyltransferase | *F. verticilloides* | trifloxystrobin | 11.61 |
| CJ | alpha-1,4-polygalactosaminidase | *F. verticilloides* | trifloxystrobin | 4.65 |
| CK | beta-1,6-glucanase | *F. verticilloides* | trifloxystrobin | 4.25 |
| CL | alpha-1,3-glucanase | *F. verticilloides* | trifloxystrobin | 2.55 |

TABLE 5-continued

| Enzyme | Activity | Target Fungus | Fungicide | % inhibition |
|--------|----------|---------------|-----------|--------------|
| CM | chitosanase | *C. gleosporoides* | antracol | 10.69 |
| | | *C. gleosporoides* | none | 29.63 |
| CN | chitin deacetylase | *C. gleosporoides* | antracol | 24.45 |
| CO | glyoxal oxidase | *C. gleosporoides* | antracol | 18.75 |

Example 6: MTT Cell Viability Assay for Determination of IC$_{50}$ for Chemical Fungicides Concentrations that result in a 50% inhibition of germination and growth (IC$_{50}$) for the chemical fungicides antracol (propineb), prothioconazole and trifloxystrobin were determined for fungal spores of *Fusarium verticilloides,* invention following, in general, the principles of the invention and including such departures from the present disclosure as come within known or customary practice within the art to which the invention pertains and as may be applied to the essential features hereinbefore set forth and as follows in the scope of the appended claims.

SEQUENCE LISTING

```
Sequence total quantity: 1
SEQ ID NO: 1          moltype = AA  length = 423
FEATURE               Location/Qualifiers
source                1..423
                      mol_type = protein
                      organism = Streptomyces griseus
SEQUENCE: 1
MFKLHRPRAR LRALAAAACT AALGATLLGV AGMSPAGATP AAQSAASPAA AEAAPTAAGD  60
KVIGYFTNWG TYDRNYHVKN IETSGSADKL THINYAFGNV IGGKCTIGDS YADYEKAYTA  120
DQSVDGVADT WDQPLRGNFN QLRKLKKLHP DLKILWSFGG WTWSGGFGQA AQNPAAFAKS  180
CRDLVEDPRW ADVFDGIDID WEYPNACGLT CDTSGRDAYG NLLGELRKSF GTDLVTSAIT  240
ADGSDGGKID AVDYAGAAKH LDWYLPMTYD FFGAWEAKGP TAPHSPLTSY PGVPTEGFNS  300
DAAISKLKSL GIPPEKLLLG IGFYGRGWTG VTRSEPGGSA TGAAAGTYEA GIEDYRVLKN  360
SCPATGKVAG TAYAHCGTDW WSYDTPETIG SKMNYKNEQG LGGTFFWELS GDTGNGELIK  420
AIR                                                                423
```

*Colletotrichum* gleosporoides or both. Assays were performed as described in Example 5, with the following exceptions. Each fungicide was dissolved in DMSO at 1 mg/mL concentration, then added to the germination assay at final concentrations of 0, 0.01, 0.02, 0.04, 0.06, 0.08 mg/mL. Fit IC$_{50}$ concentrations are shown in Table 6.

TABLE 6

| | IC$_{50}$ concentrations for various chemical fungicides on *F. verticilloides* and *C. gleosporoides* | |
|---|---|---|
| Fungicide | IC$_{50}$ for *F. verticilloides* (mg/mL) | IC$_{50}$ for *C. gleosporoides* (mg/mL) |
| Antracol (Propineb) | ~0.3 | 0.29 |
| Prothioconazole | 0.022 | 0.013 |
| Trifloxystrobin | 0.006 | 0.018 |

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the That which is claimed:

1. A composition comprising:
   a carrier;
   a polypeptide having chitinase activity and an amino acid sequence that is at least 97.5 percent identical to the amino acid sequence set forth herein as SEQ ID NO: 1; and
   one or more of propineb, benomyl, fluopyram, prothioconazole and trifloxystrobin.

2. The composition of claim 1, said polypeptide having an amino acid sequence that is at least 98 percent identical to the amino acid sequence set forth herein as SEQ ID NO: 1.

3. The composition of claim 1, said polypeptide having an amino acid sequence that is at least 98.5 percent identical to the amino acid sequence set forth herein as SEQ ID NO: 1.

4. The composition of claim 1, said polypeptide having an amino sequence that is at least 99 percent identical to the amino acid sequence set forth herein as SEQ ID NO: 1.

5. The composition of claim 1, said polypeptide having an amino sequence that is at least 99.5 percent identical to the amino acid sequence set forth herein as SEQ ID NO: 1.

6. The composition of claim 1, said polypeptide comprising the amino acid sequence set forth herein as SEQ ID NO: 1.

7. The composition of claim 1, said polypeptide being derived from a *Streptomyces griseus*.

8. The composition of claim 1, said polypeptide being present at a concentration sufficient to reduce germination and/or growth of one or more phytopathogenic fungi when said composition is applied to a plant, plant propagation material or plant growth medium.

9. The composition of claim 1, said polypeptide comprising about 0.01 percent to about 10 percent of said composition, by weight, based upon the total weight of said composition.

10. The composition of claim 1, wherein said carrier is formulated into a plurality of granules comprising said polypeptide.

11. The composition of claim 10, said plurality of granules having an average particle size of 20-2000 μm equivalent spherical diameter.

12. The of claim 10, said polypeptide being present within said plurality of granules.

13. The composition of claim 1, said carrier comprising an aqueous liquid.

14. A method comprising applying to a living plant a composition comprising:

a carrier;

a polypeptide having chitinase activity and an amino acid sequence that is at least 97.5 percent identical to the amino acid sequence set forth herein as SEQ ID NO: 1; and one or more acaricides, insecticides and/or nematicides selected from carbamates, diamides, macrocyclic lactones, neonicotinoids, organophosphates, phenylpyrazoles, pyrethrins, spinosyns, synthetic pyrethroids, tetronic acids, and tetramic acids, and/or one or more fungicides selected from benzimidazoles, benzothiadiazole, carboxamides, carboxylic acid amides, morpholines, phenylamides, phosphonates, quinone outside inhibitors, thiazolidines, thiophanates, and triazoles.

15. The method of claim 14, said composition applied in an amount sufficient to suppress and/or prevent infection of said living plant by one or more fungal pathogens.

16. A method comprising applying to a plant propagation material a composition comprising:

a carrier;

a polypeptide having chitinase activity and an amino acid sequence that is at least 97.5 percent identical to the amino acid sequence set forth herein as SEQ ID NO: 1: and one or more acaricides, insecticides and/or nematicides selected from carbamates, diamides, macrocyclic lactones, neonicotinoids, organophosphates, phenylpyrazoles, pyrethrins, spinosyns, synthetic pyrethroids, tetronic acids, and tetramic acids, and/or one or more fungicides selected from benzimidazoles, benzothiadiazole, carboxamides, carboxylic acid amides, morpholines, phenylamides, phosphonates, quinone outside inhibitors, thiazolidines, thiophanates, and triazoles.

17. The method of claim 16, said composition applied in an amount sufficient to suppress and/or prevent infection of said plant propagation material by one or more fungal pathogens.

18. A method comprising applying to a plant growth medium a composition comprising:

a carrier;

a polypeptide having chitinase activity and an amino acid sequence that is at least 97.5 percent identical to the amino acid sequence set forth herein as SEQ ID NO: 1; and one or more acaricides, insecticides and/or nematicides selected from carbamates, diamides, macrocyclic lactones, neonicotinoids, organophosphates, phenylpyrazoles, pyrethrins, spinosyns, synthetic pyrethroids, tetronic acids, and tetramic acids, and/or one or more fungicides selected from benzimidazoles, benzothiadiazole, carboxamides, carboxylic acid amides, morpholines, phenylamides, phosphonates, quinone outside inhibitors, thiazolidines, thiophanates, and triazoles.

19. The method of claim 18, said composition applied in an amount sufficient to suppress and/or prevent growth and/or reproduction of one or more fungal pathogens in said plant growth medium.

\* \* \* \* \*